US010792167B2

(12) United States Patent
Khosla et al.

(10) Patent No.: US 10,792,167 B2
(45) Date of Patent: Oct. 6, 2020

(54) SURGICAL IMPACTOR/EXTRACTOR ASSEMBLY AND METHOD OF USE

(71) Applicant: ARTHREX, INC., Naples, FL (US)

(72) Inventors: Rudraksh Khosla, Naples, FL (US); Mark A. Wise, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 58 days.

(21) Appl. No.: 15/933,797

(22) Filed: Mar. 23, 2018

(65) Prior Publication Data

US 2018/0228624 A1     Aug. 16, 2018

Related U.S. Application Data

(62) Division of application No. 14/452,656, filed on Aug. 6, 2014, now Pat. No. 9,925,066.

(60) Provisional application No. 61/865,329, filed on Aug. 13, 2013.

(51) Int. Cl.
*A61F 2/46*         (2006.01)
*A61B 17/92*      (2006.01)

(52) U.S. Cl.
CPC .............. *A61F 2/461* (2013.01); *A61B 17/92* (2013.01); *A61F 2002/4625* (2013.01)

(58) Field of Classification Search
CPC ......... A61B 17/1767; B25B 9/04; B25B 9/00; B25B 1/2489; B25B 5/003; A61F 2/46; A61F 2002/4625; A61F 2/461
USPC .......................................................... 606/99
See application file for complete search history.

(56) References Cited

U.S. PATENT DOCUMENTS

| 618,640 | A | | 1/1899 | Burk |
|---|---|---|---|---|
| 3,306,646 | A | | 2/1967 | Flora, Jr. |
| 3,978,605 | A | | 9/1976 | Maruniak |
| 5,059,196 | A | | 10/1991 | Coates |
| 5,169,132 | A | | 12/1992 | Myers et al. |
| 5,417,693 | A | | 5/1995 | Sowden et al. |
| 5,732,992 | A | * | 3/1998 | Mauldin ................. A61F 2/461 |
| | | | | 269/134 |
| 6,098,972 | A | | 8/2000 | Klimach et al. |
| 6,458,022 | B1 | | 10/2002 | Folz |
| 7,234,376 | B2 | | 6/2007 | Bader |
| 7,338,497 | B2 | | 3/2008 | Coon et al. |
| 7,950,636 | B2 | | 5/2011 | Kinnison et al. |
| 8,286,955 | B2 | | 10/2012 | Damang |
| 2012/0143204 | A1 | | 6/2012 | Blaylock et al. |

FOREIGN PATENT DOCUMENTS

DE            10013331          9/2001

OTHER PUBLICATIONS

Extended European Search Report for Application No. EP 14 18 0723 dated Oct. 20, 2014.

* cited by examiner

*Primary Examiner* — David W Bates
(74) *Attorney, Agent, or Firm* — Carlson, Gaskey & Olds

(57) ABSTRACT

A surgical assembly includes a housing, a first arm extending outside the housing and a linkage assembly housed by the housing and connected to the first arm. Movement of the linkage assembly inside the housing is linked to movement of the first arm outside of the housing.

19 Claims, 11 Drawing Sheets

SURGICAL IMPACTOR/EXTRACTOR ASSEMBLY AND METHOD OF USE

CROSS-REFERENCE TO RELATED APPLICATION

This is a divisional of U.S. patent application Ser. No. 14/452,656, filed on Aug. 6, 2014, which claims priority to U.S. Provisional Application No. 61/865,329, filed on Aug. 13, 2013, the entire disclosures of which are incorporated by reference herein.

BACKGROUND

This disclosure relates to orthopedic surgical instrumentation, and more particularly to a surgical impactor/extractor assembly and method of use for installing and/or removing a prosthetic device, such as a femoral implant or trial.

Total or partial knee arthroplasty has been performed for many years to treat patients with diseased knee joints. Numerous cuts (i.e., resections) must be made in the femur to prepare the femur for receiving a prosthetic device. Surgical tools may be necessary for installing and/or removing prosthetic devices. Although impactor/extractor tools are known, additional advances in this field of technology are desired.

SUMMARY

A surgical assembly according to an exemplary aspect of the present disclosure includes, among other things, a housing, a first arm extending outside the housing and a linkage assembly housed by the housing and connected to the first arm. Movement of a portion of the linkage assembly inside the housing is linked to movement of the first arm outside of the housing.

In a further non-limiting embodiment of the foregoing assembly, the portion of the linkage assembly is movable in a vertical direction to move the first arm in a horizontal direction.

In a further non-limiting embodiment of either of the foregoing assemblies, a second arm is mounted inside the housing. The first arm and the second arm move in opposite directions in response to movement of the portion of the linkage assembly.

In a further non-limiting embodiment of any of the foregoing assemblies, the linkage assembly includes a first link and a second link.

In a further non-limiting embodiment of any of the foregoing assemblies, the first link is connected between an adjustment bar or a glide sleeve and the second link, and the second link is connected between the first link and the first arm.

In a further non-limiting embodiment of any of the foregoing assemblies, a dial is mounted inside the housing and is rotatable to move an adjustment block toward or away from the housing.

In a further non-limiting embodiment of any of the foregoing assemblies, a dial is mounted outside the housing and is rotatable to move an adjustment block toward or away from the housing.

In a further non-limiting embodiment of any of the foregoing assemblies, the linkage assembly includes at least one link that travels between opposing ends of a slot of the housing during movement of the first arm.

In a further non-limiting embodiment of any of the foregoing assemblies, a portion of the first arm protrudes from the housing and is connectable to a prosthetic device.

In a further non-limiting embodiment of any of the foregoing assemblies, a lever is movable to lock or unlock the first arm relative to the housing.

A surgical assembly according to another exemplary aspect of the present disclosure includes, among other things, a housing, a first arm that protrudes from a first side of the housing, a second arm that protrudes from a second side of the housing, and a linkage assembly connected to the first arm and the second arm and configured to move the first arm and the second arm between a first position farther away from the housing and a second position closer to the housing.

In a further non-limiting embodiment of any of the foregoing assemblies, the linkage assembly includes a central rod, a glide sleeve, a first link and a second link housed inside the housing.

In a further non-limiting embodiment of any of the foregoing assemblies, the linkage assembly includes an adjustment bar, a first link, a second link, and a biasing member.

In a further non-limiting embodiment of any of the foregoing assemblies, the linkage assembly includes an actuator movable in a vertical direction to move the first arm and the second arm in opposite horizontal directions.

In a further non-limiting embodiment of any of the foregoing assemblies, a lever is movable to lock or unlock at least one of the first arm and the second arm relative to the housing.

A surgical method according to another exemplary aspect of the present disclosure includes, among other things, moving a portion of a surgical assembly in a first direction and moving an arm of the surgical assembly in a second, different direction in response to the step of moving the portion to configure the surgical assembly for connection to a prosthetic device.

In a further non-limiting embodiment of the foregoing method, the moving step includes either moving an actuator or moving a glide sleeve in the first direction.

In a further non-limiting embodiment of either of the foregoing methods, the method includes positioning the surgical assembly relative to the prosthetic device and moving the arm from an expanded position to a collapsed position to connect the arm to the prosthetic device.

In a further non-limiting embodiment of any of the foregoing methods, the method includes tightening or loosening an adjustment block of the surgical assembly relative to the prosthetic device.

In a further non-limiting embodiment of any of the foregoing methods, the method includes using the surgical assembly to insert the prosthetic device into a joint or using the surgical assembly to remove the prosthetic device from the joint.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Figure 1:
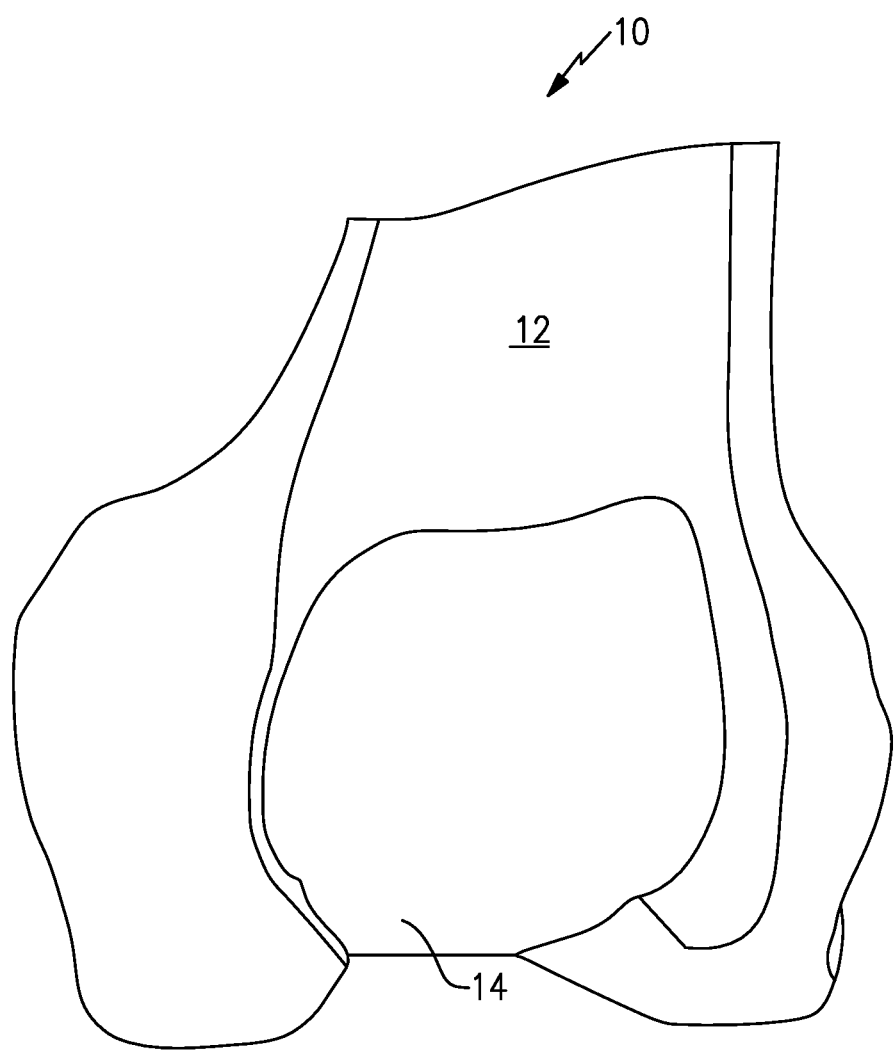
FIG. 1 schematically illustrates a knee joint that includes a prosthetic device.

FIG. 1 illustrates a portion of a joint 10, such as the knee joint of a human body. The joint 10 includes a femur 12, but could include other or additional bones, including but not limited to, a tibia and a patella (not shown). Diseased portions of the femur 12 have been removed and replaced with a prosthetic device 14 that is positionable within the joint 10. In one embodiment, the prosthetic device 14 is a femoral implant. In another embodiment, the prosthetic device 14 is a trial that may be used to confirm the appropriate size of a femoral implant. The prosthetic device 14 may be of any size, shape or configuration and is patient specific.

This disclosure is directed to surgical impactor/extractor assemblies that can be used to insert and/or extract the prosthetic device 14 into/from the joint 10. Although the embodiments of this disclosure are presented in the context of implanting/removing a femoral implant or trial into/from a knee joint, this disclosure could extend to other implants and to other surgeries.

Figure 2:
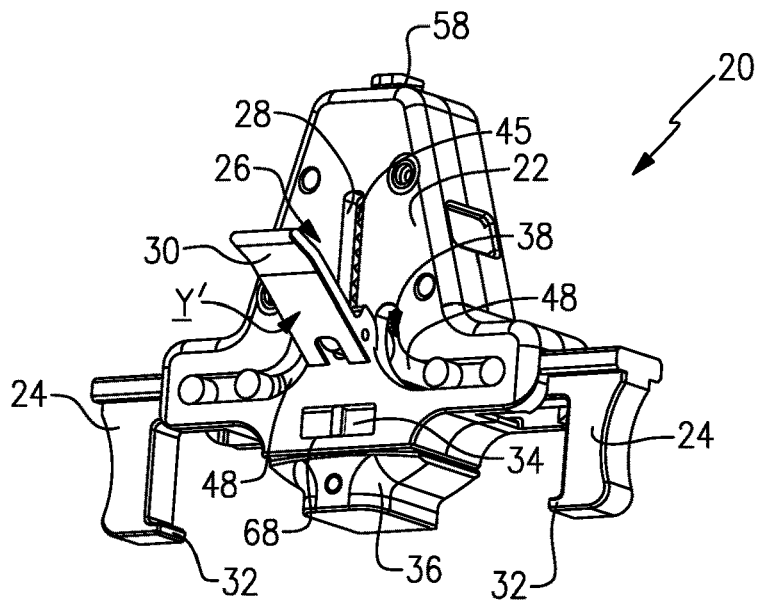
FIG. 2 illustrates a surgical impactor/extractor assembly.
Figure 3:
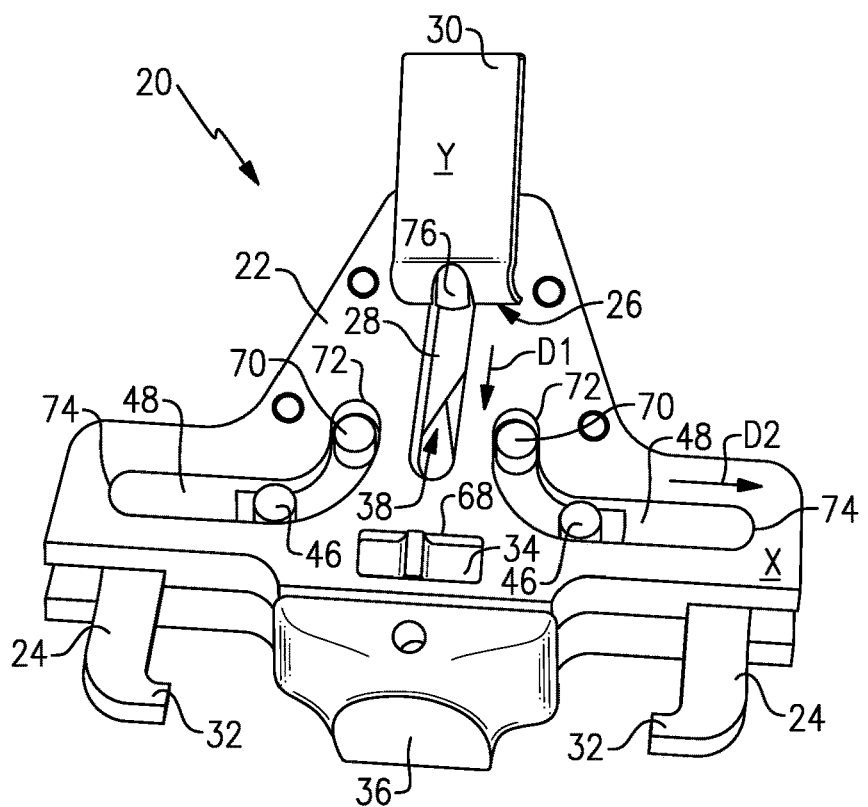
FIG. 3 illustrates a first positioning of arms of a surgical impactor/extractor assembly.
Figure 4:
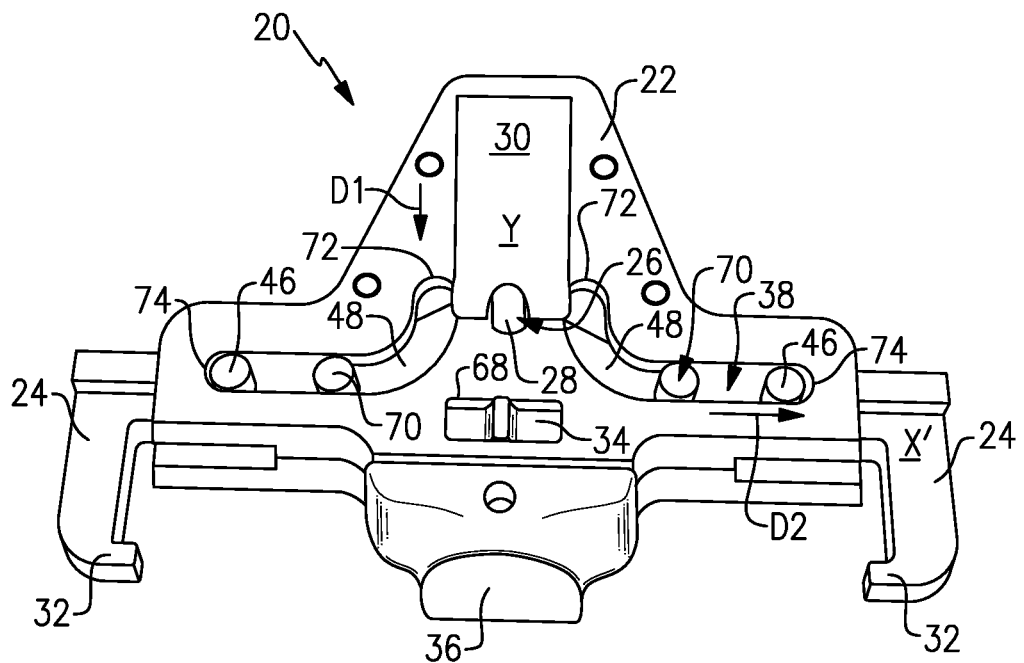
FIG. 4 illustrates a second positioning of arms of a surgical impactor/extractor assembly.

FIGS. 2, 3 and 4 illustrate a surgical impactor/extractor assembly 20 that may be used to either insert or extract a prosthetic device. The surgical impactor/extractor assembly 20 may include a housing 22, one or more arms 24 (two arms are included in one non-limiting embodiment), and an actuator or first portion 26 for moving the arms 24 relative to the housing 22 in order to connect the surgical impactor/extractor assembly 20 to a prosthetic device.

The housing 22 may embody any of a variety of shapes and can include either a unitary structure or multiple parts. The size and shape illustrated in these figures is not intended to limit this disclosure. The housing 22 may additionally include multiple openings, slots, formations, retaining features etc. for accommodating the other parts of the surgical impactor/extractor assembly 20. In one embodiment, the housing 22 is made of a metallic material, such as stainless steel, although other materials are also contemplated.

In one non-limiting embodiment, two arms 24 are mounted inside the housing 22. The arms 24 may be generally L-shaped and include tabs 32 for connecting to pockets of a prosthetic device (see, for example, FIGS. 9, 10 and 11). At least a portion of each arm 24 protrudes from the housing 22 in order to connect to a prosthetic device.

In one embodiment, the arms 24 are moveable between a first position X (see FIG. 3) and a second position X' (see FIG. 4) relative to the housing 22. The first position of the arms 24 is a collapsed position and the second position is an expanded position. Of course, the arms 24 could also be moved to any position between the first position X and the second position X'.

Movement of the arms 24 is guided by slots 48 that are formed in the housing 22. For example, the slots 48 provide a track for guiding movement of a linkage assembly 38 that is connected between the arms 24 and the actuator 26, as is further discussed below. In one embodiment, the slots 48 are curved slots.

The actuator 26, which may be part of the linkage assembly 38, is moveable in a first direction D1 in order to move the arms in a second direction D2. In other words, vertical movement of the actuator 26 may be transferred to horizontal movement of the arms 24. In one embodiment, the direction D2 is perpendicular to the direction D1.

The actuator 26 is moveable within another slot 28 formed in the housing 22. In one embodiment, the actuator 26 includes a cam lever 30 that is moveable between a locked position Y (see FIGS. 3 and 4) and an unlocked position Y' (see FIG. 2). In the locked position Y, the cam lever 30 is pressed against the housing 22 and is parallel thereto. The cam lever 30 is moved away from the housing 22 to a non-parallel position in the unlocked position. The cam lever 30 may be rotated to the unlocked position Y' in order to release the actuator 26 for movement within the slot 28, or may be flipped to the locked position Y in order to lock the actuator 26 and maintain a positioning of the arms 24 relative to the housing 22.

A dial or second portion 34, such as a threaded knob, may be rotatably mounted inside the housing 22. The dial 34 partially protrudes from a window 68 of the housing 22 so that it can be accessed by a surgeon or other user. In one embodiment, the dial 34 is turned, either in a clockwise or counter-clockwise direction, in order to move an adjustment block 36 either toward or away from a prosthetic device. In other words, rotary movement of the dial 34 is transferred to linear movement of the adjustment block 36, such as through a threaded pin (not shown), in order to loosen or tighten the grip of the surgical impactor/extractor assembly 20 on a prosthetic device.

Figure 5:
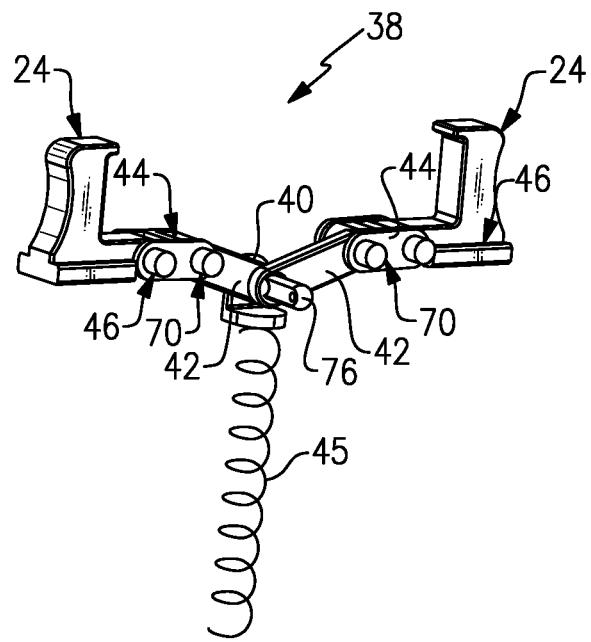
FIG. 5 illustrates a linkage assembly of a surgical impactor/extractor assembly.

Referring to FIG. 5, with continued reference to FIGS. 2, 3 and 4, the linkage assembly 38 of the surgical impactor/extractor assembly 20 is housed within the housing 22 and connects between the actuator 26 and the arms 24 to link movement of the actuator 26 with movement of the arms 24. For example, the linkage assembly 38 transfers movement of the actuator 26 in the first direction D1 to the arms 24 in order to move the arms 24 in the second direction D2, or to any position between the first and second positions X, X'.

In one embodiment, the linkage assembly 38 includes an adjustment bar 40, links 42, H-links 44, and a biasing member 45. The H-links 44 are connected at a first end to the arms 24 by one or more pins 46 and at a second end to the links 42 by additional pins 70. The links 42 extend between the H-links 44 and the adjustment bar 40. The links 42 may be received by a rod 76 that protrudes from the adjustment bar 40. The cam lever 30 of the actuator 26 may be pinned to the rod 76 (see FIG. 3). The biasing member 45, which may be spring, biases the linkage assembly 38 toward either the first position X or the second position X' of the arms 24.

In operation, movement of cam lever 30 of the actuator 26 is transferred through the adjustment bar 40, then through the links 42, and then through the H-links 44 in order to move the arms 24. In one embodiment, the slots 48 of the housing 22 guide movement of the H-links 44 of the linkage assembly 38. The pins 46, 70 travel between opposing ends 72, 74 of the slots 48 to guide the arms 24 between the first position X and the second position X'. The pins 70 may strike the end 72 to limit further travel of the arms 24 beyond the first position X. Similarly, the pins 46 may strike the end 74 to limit further travel of the arms 24 beyond the second position X'. The slots 48 can be designed to provide any amount of travel between the first position X and the second position X'.

Figure 6:
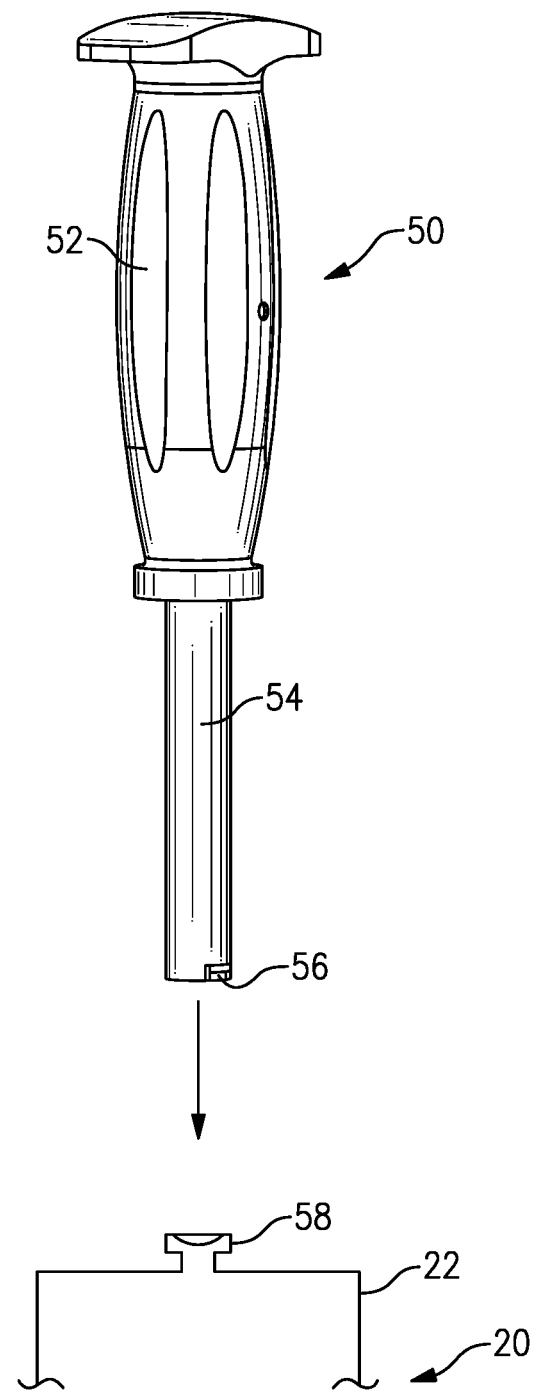
FIG. 6 illustrates a handle of a surgical impactor/extractor assembly.

FIG. 6 illustrates a handle 50 that can be utilized with the surgical impactor/extractor assembly 20 of FIGS. 2-5. The handle 50 includes a grip 52 and a shaft 54 that extends from the grip 52. A slot 56 may be formed at a distal end of the shaft 54 for connecting the handle 50 to the housing 22 of the surgical impactor/extractor assembly 20. In one embodiment, the slot 56 is a T-slot that may be connected relative to a key seat feature 58 that extends from the housing 22.

The key seat feature 58 may extend from a portion of the housing 22 that is on an opposite side from the adjustment block 36 (see FIG. 2). In one non-limiting embodiment, the handle 50 is attached to the housing 22 by inserting the key seat feature 58 into the slot 56 of the handle 50 and then rotating the handle 50 to lock it in position relative to the key seat feature 58.

FIGS. 7-13, with continued reference to FIGS. 1-6, schematically illustrate a method for utilizing a surgical impactor/extractor assembly 20 to either insert or extract a prosthetic device 14 into/from a joint. In one non-limiting embodiment, the surgical impactor/extractor assembly 20 is used to insert or extract a femoral implant or trial during a total knee arthroplasty procedure. However, the surgical impactor/extractor assembly 20 could be used for other procedures within the scope of this disclosure. In addition, it should be understood that fewer or additional steps than are recited below could be performed and that the recited order of steps is not intended to limit this disclosure.

Figure 7:
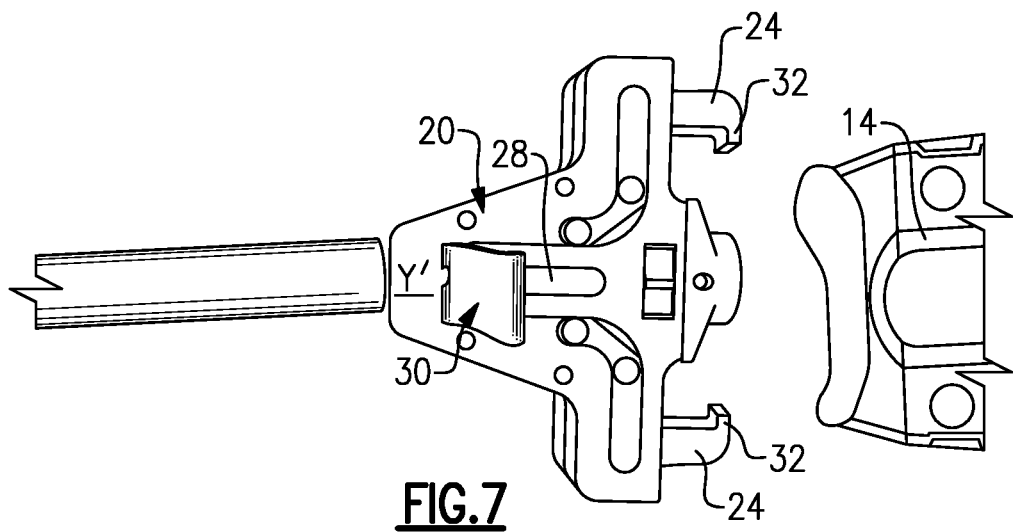
FIGS. 7, 8, 9, 10, 11, 12 and 13 schematically illustrate a method of using a surgical impactor/extractor assembly to either implant or extract a prosthetic device into/from a joint.
Figure 8:
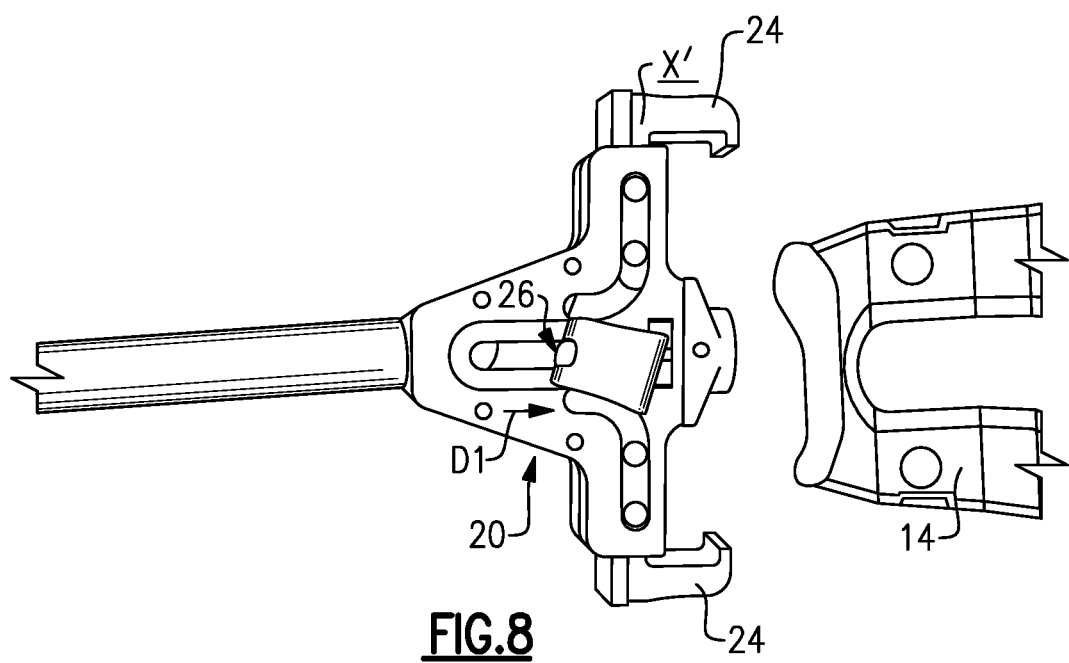

As illustrated by FIG. 7, the cam lever 30 of the actuator 26 may be pivoted to the unlocked position Y' to prepare to move the arms 24 into a position acceptable to connect to a prosthetic device 14. Once unlocked, the actuator 26 can be moved in the first direction D1 to move the arms 24 to an expanded position X' (see FIG. 8). The surgical impactor/extractor assembly 20 may then be positioned relative to the prosthetic device 14.

Figure 9:
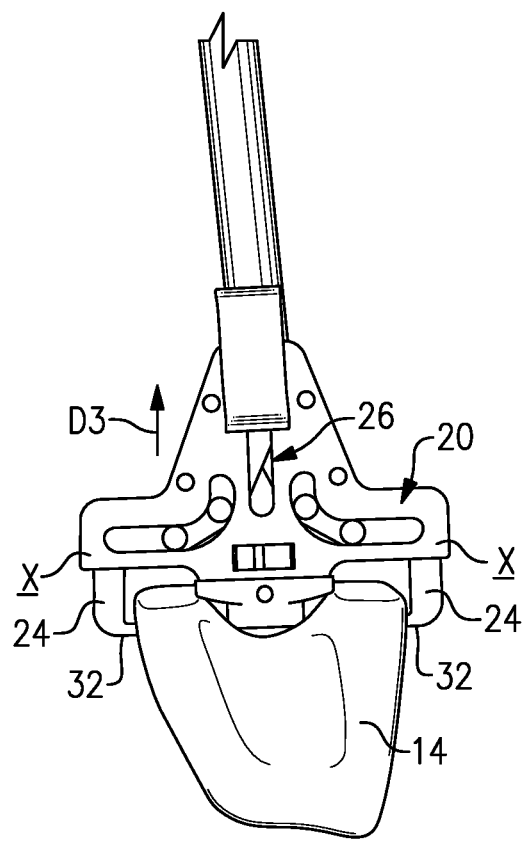
Figure 10:
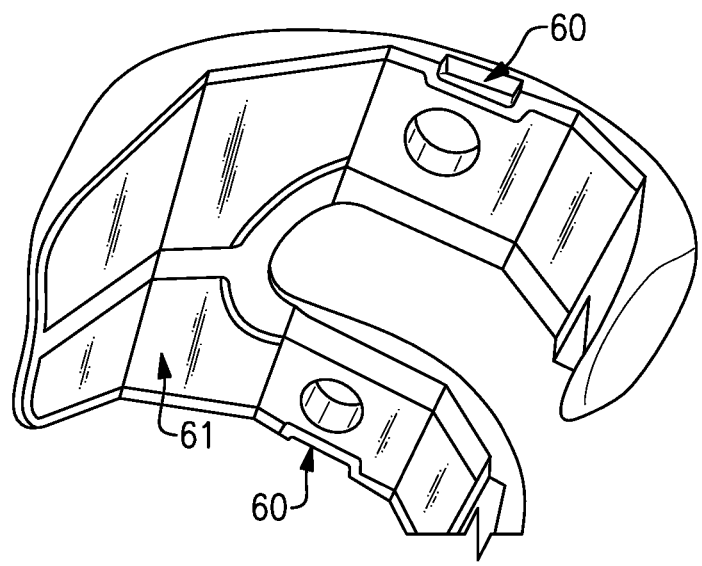
Figure 11:
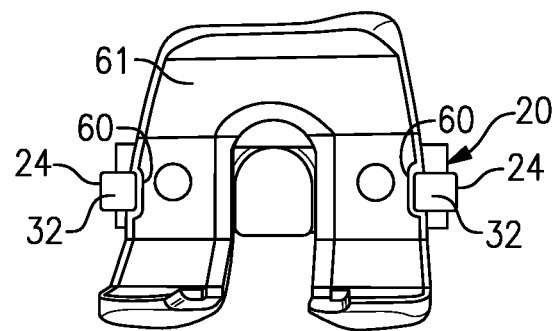

Referring to FIG. 9, the actuator 26 is next moved in a direction D3 that is opposite of the first direction D1 to collapse the arms 24 to the first position X such that the arms 24 connect to the prosthetic device 14. As shown in FIG. 10, the prosthetic device 14 includes one or more pockets 60 on its underside 61 that can receive the tabs 32 of the arms 24. Proper positioning of the tabs 32 relative to the pockets 60 is illustrated by FIG. 11.

Figure 12:
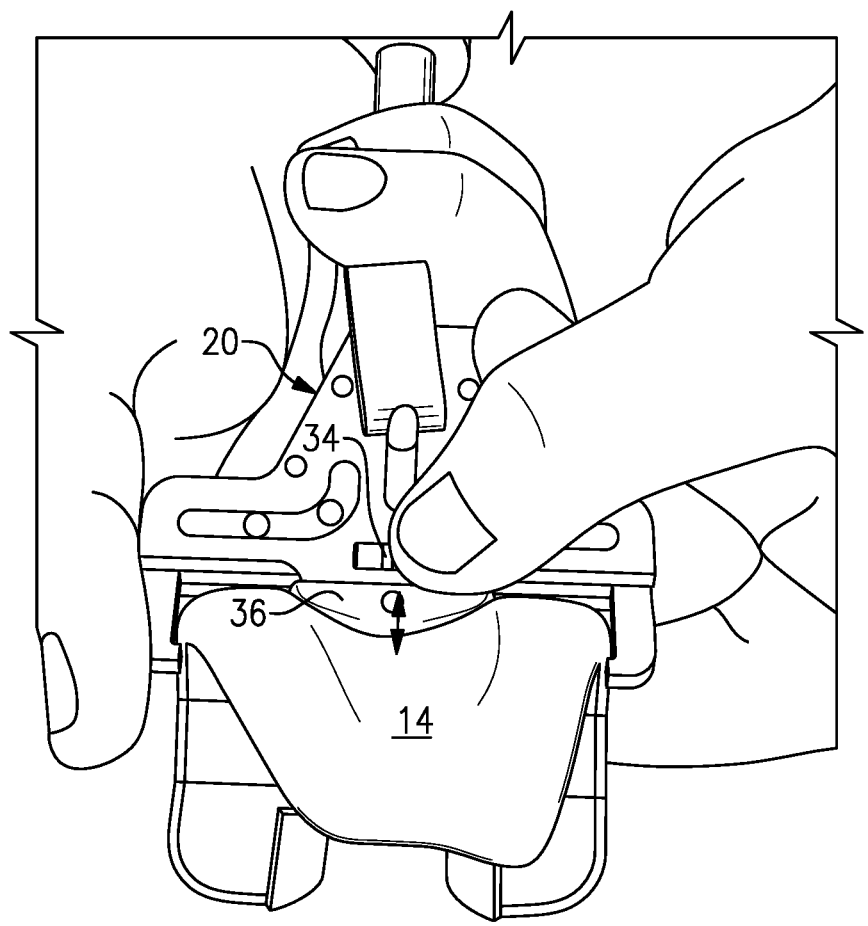
Figure 13:
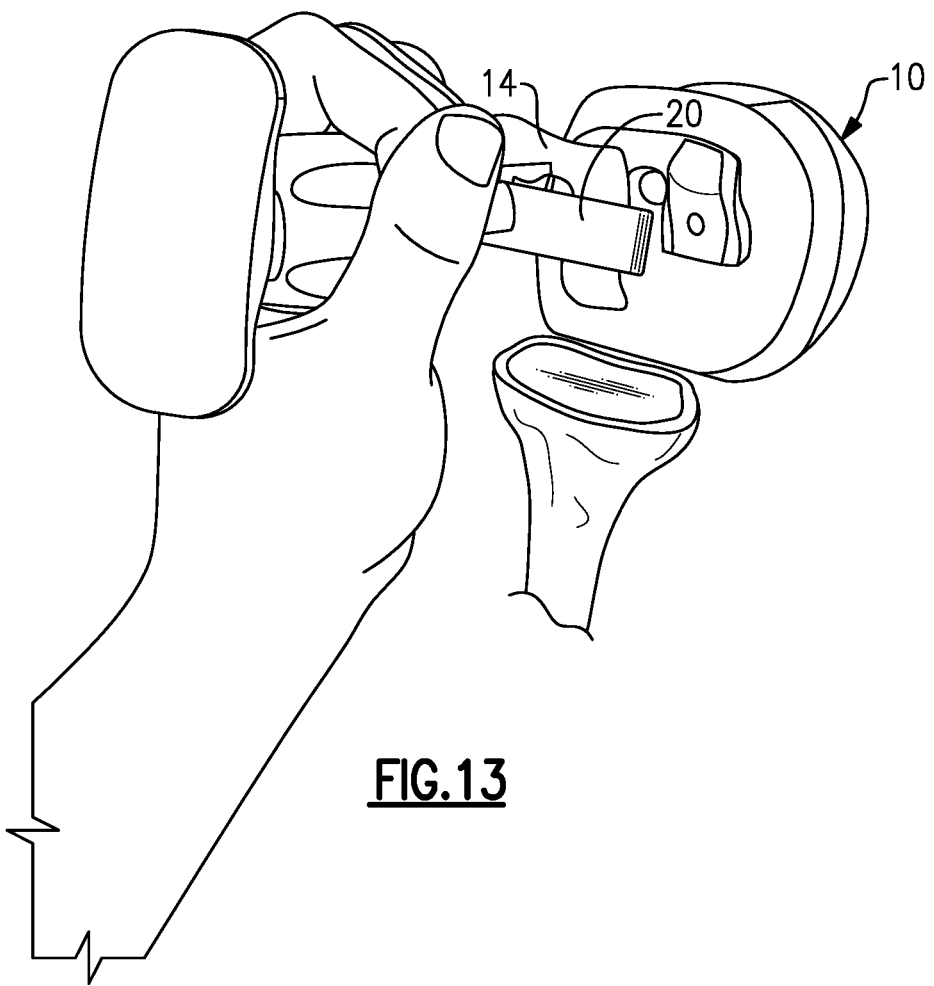

Once the arms 24 are properly positioned to hold the prosthetic device 14, the dial 34 may be rotated in order to tighten or loosen the adjustment block 36 relative to the prosthetic device 14 (see FIG. 12). Thereafter, as shown in FIG. 13, the surgical impactor/extractor assembly 20 may be used to either insert the prosthetic device 14 or remove it from a joint 10, such as a knee joint.

Figure 14:
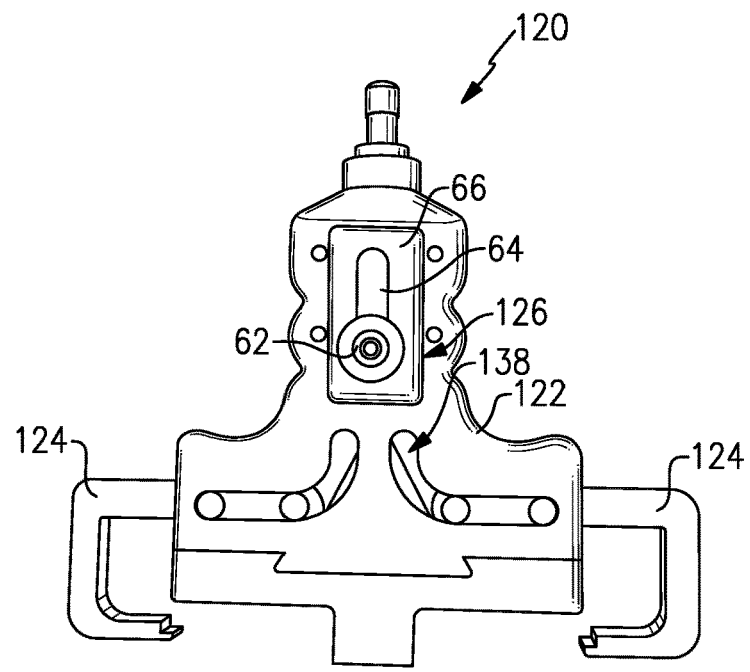
FIG. 14 illustrates a second embodiment of a surgical impactor/extractor assembly.
Figure 15:
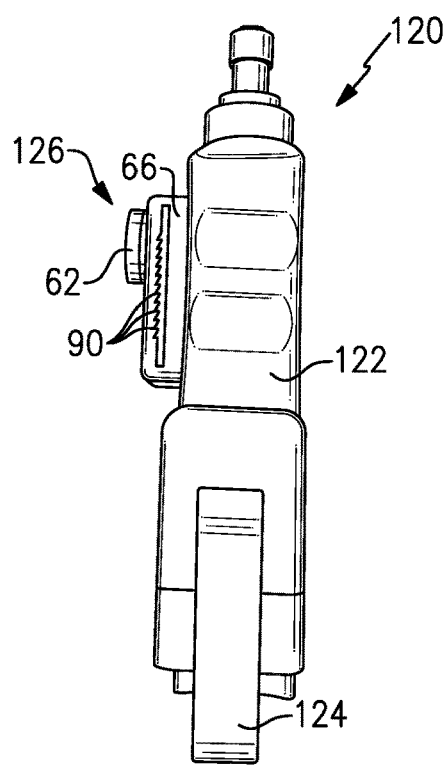
FIG. 15 illustrates a side view of the surgical impactor/extractor assembly of FIG. 14.

FIGS. 14 and 15 illustrate a second embodiment of a surgical impactor/extractor assembly 120. In this disclosure, like reference numerals designate like elements where appropriate and reference numerals with the addition of 100 or multiples thereof designate modified elements that are understood to incorporate the same features and benefits of the corresponding original elements.

The assembly 120 is similar to the assembly 20 but includes a different actuator 126. In this embodiment, the actuator 126 includes a button 62 that may be moved within a slot 64 of a cover 66 in order to effectuate movement of the arms 124 to the expanded position illustrated by FIG. 14. The cover 66 may be attached to a housing 122 of the assembly 120. A linkage assembly 138 transfers movement of the button 62 to the arms 124.

As best shown in FIG. 15, the cover 66 may include a plurality of teeth 90 for locking a positioning of the button 62 relative to the housing 122. The button 62 can be moved in and out of engagement with the teeth 90 to lock and release the actuator 126 for controlling a positioning of the arms 124. The assembly 120 can be used in a method that is similar to the one described with reference to FIGS. 7-13 in order to implant/extract a prosthetic device.

Figure 16:
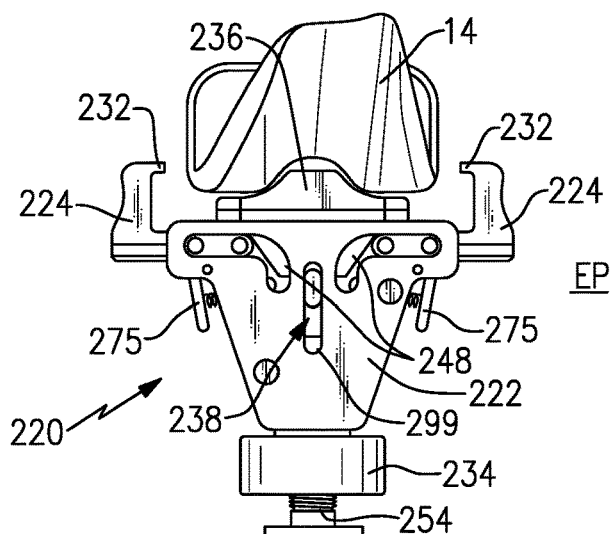
FIGS. 16 and 17 illustrate a third embodiment of a surgical impactor/extractor assembly.
Figure 16:
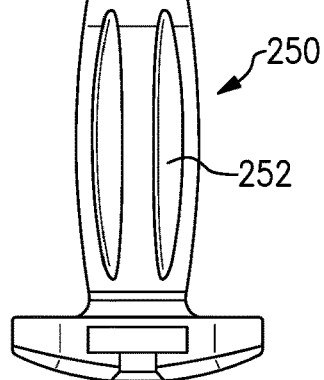
Figure 17:
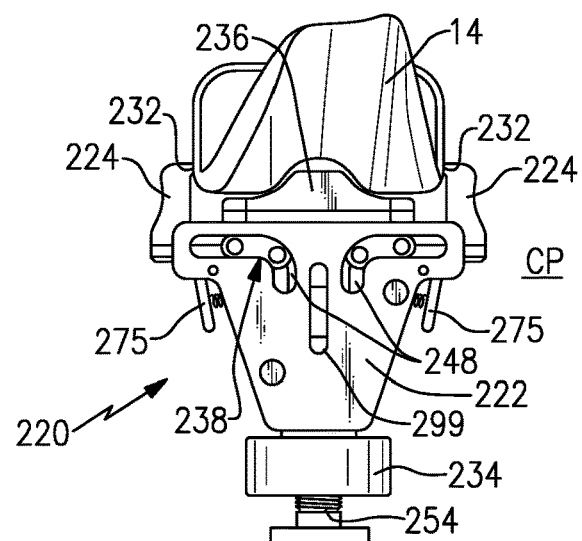
Figure 17:
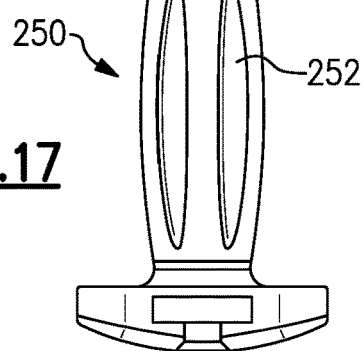

FIGS. 16 and 17 illustrate yet another impactor/extractor assembly 220 that can be used to insert or extract a prosthetic device 14. The impactor/extractor assembly 220 may include a housing 222, arms 224, a dial 234 and a handle 250. In one non-limiting embodiment, the arms 224 are generally L-shaped and at least partially protrude outside of the housing 222. The arms 224 may include tabs 232 for engaging pockets of the prosthetic device 14. In one embodiment, the arms 224 are moveable between the expanded position EP of FIG. 16 and the collapsed position CP of FIG. 17 relative to the housing 222 to disconnect/connect to the prosthetic device 14.

Movement of the arms 224 may be guided by slots 248 that are formed in the housing 222. For example, the slots 248 provide a track for guiding movement of a linkage assembly 238 that is connected between the arms 224 and a central rod 299, as is further discussed below.

The dial 234 may be rotatably mounted to the housing 222. In one embodiment, the dial 234 is turned, either in a clockwise or counter-clockwise direction, in order to move an adjustment block 236 either toward or away from the prosthetic device 14. In other words, rotary movement of the dial 234 may be transferred to linear movement of the adjustment block 236 through the central rod 299 in order to loosen or tighten the grip of the surgical impactor/extractor assembly 220 on the prosthetic device 14. In one embodiment, rotary movement of the dial 234 advances a threaded portion 297 of the central rod 299 in a direction V1 (see FIG. 19), which is generally toward the prosthetic device 14.

The handle 250 may include a grip 252 and a shaft 254 that extends from the grip 252. The shaft 254 may engage the dial 234 to connect the handle 250 to the housing 222 of the surgical impactor/extractor assembly 220. In one embodiment, the shaft 254 is welded to the dial 234. However, the handle 250 could be connected to the dial 234, or to another portion of the housing 222, in any known manner.

The impactor/extractor assembly 220 may additionally include one or more levers 275 that are connected to the housing 222. The levers 275 can engage the arms 224 in a variety of positions to lock movement of the arms 224 relative to the housing 222.

Figure 18:
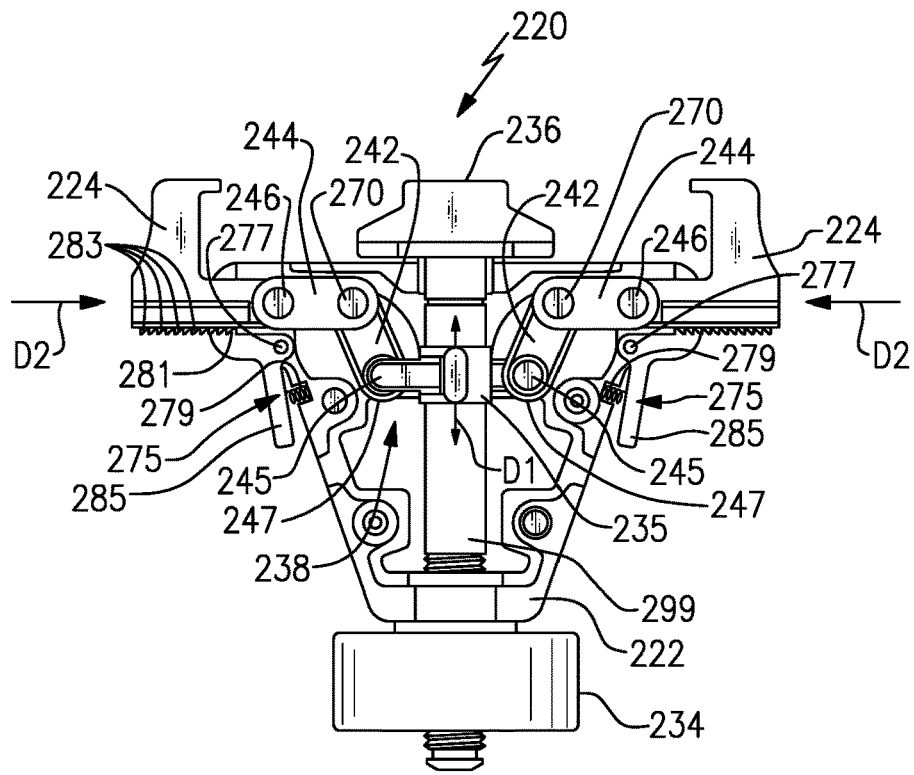
FIGS. 18 and 19 illustrate additional features of the surgical impactor/extractor assembly of FIGS. 16 and 17.
Figure 19:
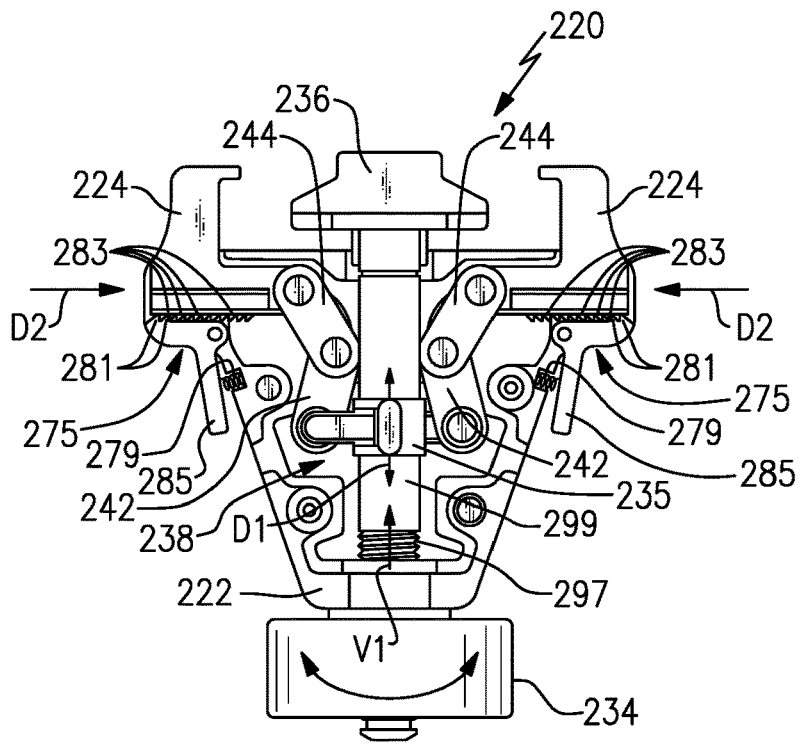

Additional details concerning the linkage assembly 238 and the levers 275 of the impactor/extractor assembly 220 are illustrated in the cross-sectional views of FIGS. 18 and 19. In one embodiment, the linkage assembly 238 includes the central rod 299, a glide sleeve 235, links 242, and H-links 244. The H-links 244 are connected at a first end to the arms 224 by one or more pins 246 and at a second end to the links 242 by additional pins 270. The links 242 extend between the H-links 244 and the glide sleeve 235. The links 42 may include openings 247 for receiving pins 245 of the glide sleeve 235. The glide sleeve 235 is received over the central rod 299 and may travel vertically along the length of the central rod 299 to move the linkage assembly 238.

For example, movement of the glide sleeve 235 in a first direction D1 moves the arms 224 in a second direction D2. In other words, vertical movement of the glide sleeve 235 may be transferred to horizontal movement of the arms 224. In one embodiment, the direction D2 is perpendicular to the direction D1. The slots 248 of the housing 222 (see FIGS. 16 and 17) guide the movement of the H-links 244 of the linkage assembly 238 to guide the arms 224 between the expanded and collapsed positions.

In one embodiment, the levers 275 are mounted to the housing 222 via pins 277. The levers 275 may be biased, with a spring 279, toward the arms 224 such that teeth 281 of the levers 275 engage corresponding teeth 283 of the arms 224. In the engaged or biased position, the levers 275 lock the positioning of the arms 224 by engaging the teeth 281, 283 together. In another embodiment, the levers 275 may be actuated or tripped to release the teeth 281, 283 from one another and allow movement of the arms 224. For example, legs 285 of the levers 275 may be pressed inwardly toward the housing 222 to overcome the biasing force of the springs 279, thereby releasing the teeth 281, 283 from one another to allow the arms 224 to move horizontally to a desired position.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method, comprising:
   linearly moving an actuator of a surgical impactor/extractor assembly in a first direction;
   moving each of a first arm and a second arm of the surgical impactor/extractor assembly from a collapsed position to an expanded position in response to linearly moving the actuator in the first direction;
   positioning the surgical impactor/extractor assembly relative to a prosthetic device;
   moving the actuator in a second direction that is opposite to the first direction;
   collapsing the first arm and the second arm against the prosthetic device in response to moving the actuator in the second direction;
   tightening or loosening an adjustment block of the surgical impactor/extractor assembly relative to the prosthetic device; and
   inserting the prosthetic device into a joint or removing the prosthetic device from the joint,
   wherein movement of the first arm is guided via a linkage assembly within a first slot formed in a housing of the surgical impactor/extractor assembly, and movement of the second arm is guided via the linkage assembly within a second slot formed in the housing.

2. The method as recited in claim 1, wherein linearly moving the actuator in the first direction includes:
   unlocking the actuator; and
   sliding the actuator in the first direction within a third slot formed in the housing of the surgical impactor/extractor assembly.

3. The method as recited in claim 2, wherein linearly moving the actuator in the second direction includes:
   sliding the actuator in the second direction within the third slot.

4. The method as recited in claim 1, wherein moving the first arm and the second arm includes:
   moving the first arm and the second arm apart from one another in directions that are perpendicular to the first direction.

5. The method as recited in claim 1, wherein collapsing the first arm and the second arm against the prosthetic device:
   engaging pockets on an underside of the prosthetic device with tabs of the first arm and the second arm.

6. The method as recited in claim 1, wherein the prosthetic device is a femoral implant or a trial.

7. The method as recited in claim 1, wherein the linkage assembly includes the actuator, a first link, a second link, a third link, and a fourth link.

8. The method as recited in claim 7, wherein movement of the actuator is transferred through the second link and then through the first link to move the first arm, and wherein movement of the actuator is transferred through the fourth link and then through the third link to move the second arm.

9. The method as recited in claim 1, wherein the first slot and the second slot are curved slots that guide movement of linkages of the linkage assembly.

10. The method as recited in claim 1, wherein the linkage assembly includes a plurality of non-threaded linkages.

11. A method, comprising:
    linearly moving an actuator of a surgical impactor/extractor assembly in a first direction;
    moving each of a first arm and a second arm of the surgical impactor/extractor assembly from a collapsed position to an expanded position in response to linearly moving the actuator in the first direction;
    positioning the surgical impactor/extractor assembly relative to a prosthetic device;
    moving the actuator in a second direction that is opposite to the first direction;
    collapsing the first arm and the second arm against the prosthetic device in response to moving the actuator in the second direction;
    tightening or loosening an adjustment block of the surgical impactor/extractor assembly relative to the prosthetic device; and
    inserting the prosthetic device into a joint or removing the prosthetic device from the joint,
    wherein tightening or loosening the adjustment block includes:

rotating a dial of the surgical impactor/extractor assembly to move the adjustment block.

12. A method, comprising:

moving an actuator of a surgical impactor/extractor assembly in a first direction;

moving each of a first arm and a second arm of the surgical impactor/extractor assembly from a collapsed position to an expanded position in response to moving the actuator in the first direction;

positioning the surgical impactor/extractor assembly relative to a prosthetic device;

moving the actuator in a second direction that is opposite to the first direction;

collapsing the first arm and the second arm against the prosthetic device in response to moving the actuator in the second direction;

tightening or loosening an adjustment block of the surgical impactor/extractor assembly relative to the prosthetic device; and inserting the prosthetic device into a joint or removing the prosthetic device from the joint, wherein the surgical impactor/extractor assembly includes a linkage assembly including the actuator, a first link, a second link, a third link, and a fourth link, wherein movement of the actuator is transferred through the second link and then through the first link to move the first arm, and wherein movement of the actuator is transferred through the fourth link and then through the third link to move the second arm, wherein movement of the first link and the second link is guided by a slot formed in a housing of the surgical impactor/extractor assembly, and wherein movement of the third link and the fourth link is guided by a second slot formed in the housing of the surgical impactor/extractor assembly.

13. A method, comprising:

moving a first portion of a surgical assembly in a first direction relative to a housing of the surgical assembly;

moving an arm of the surgical assembly that is operably connected to the first portion in a second, different direction relative to the housing in response to the step of moving the first portion to configure the surgical assembly for connection to a prosthetic device; and tightening or loosening an adjustment block of the surgical assembly relative to the prosthetic device, wherein tightening or loosening the adjustment block includes rotating, relative to the housing, a second portion of the surgical assembly that is operably connected to the adjustment block to move the adjustment block.

14. The method as recited in claim 13, wherein moving the first portion includes:

moving an actuator of the first portion in the first direction relative to the housing of the surgical assembly; or moving a glide sleeve of the first portion in the first direction relative to the housing.

15. The method as recited in claim 13, comprising:

positioning the surgical assembly relative to the prosthetic device; and moving the arm from an expanded position to a collapsed position to connect the arm to the prosthetic device.

16. The method as recited in claim 13, wherein the second portion is a dial.

17. The method as recited in claim 13, comprising one of:

using the surgical assembly to insert the prosthetic device into a joint; or using the surgical assembly to remove the prosthetic device from the joint.

18. The method as recited in claim 13, wherein the prosthetic device is a femoral implant or a trial.

19. The method as recited in claim 13, wherein the surgical assembly includes the housing, the arm, and a linkage assembly housed within the housing, and the arm protrudes outside of the housing.

* * * * *